United States Patent
Eddy

(10) Patent No.: US 8,025,120 B2
(45) Date of Patent: Sep. 27, 2011

(54) STETHOSCOPE AND ANTIMICROBIAL COVER

(76) Inventor: Patrick E. Eddy, Allendale, MI (US)

( * ) Notice: Subject to any disclaimer, the term of this patent is extended or adjusted under 35 U.S.C. 154(b) by 0 days.

(21) Appl. No.: 12/703,050

(22) Filed: Feb. 9, 2010

(65) Prior Publication Data

US 2010/0326765 A1 Dec. 30, 2010

Related U.S. Application Data

(60) Provisional application No. 61/220,641, filed on Jun. 26, 2009.

(51) Int. Cl.
*A61B 7/02* (2006.01)

(52) U.S. Cl. ......... 181/131; 181/135; 128/864; 128/865

(58) Field of Classification Search .................. 181/131, 181/135; 128/864, 865
See application file for complete search history.

(56) References Cited

U.S. PATENT DOCUMENTS

| | | | |
|---|---|---|---|
| 5,466,898 A | 11/1995 | Gilbert et al. | |
| 5,592,946 A * | 1/1997 | Eddy ............................. | 600/528 |
| 6,186,957 B1 * | 2/2001 | Milam .......................... | 600/528 |
| 6,420,455 B1 * | 7/2002 | Landgrebe et al. ........... | 523/122 |
| 6,520,281 B1 | 2/2003 | Deslauriers et al. | |
| 6,575,917 B2 | 6/2003 | Giroux et al. | |
| 2002/0170771 A1 * | 11/2002 | Milam et al. .................. | 181/131 |
| 2005/0187580 A1 * | 8/2005 | Skiba .............................. | 607/2 |
| 2007/0042198 A1 * | 2/2007 | Schonemyr et al. .......... | 428/447 |
| 2007/0193822 A1 | 8/2007 | Statner et al. | |
| 2008/0166384 A1 | 7/2008 | Jones | |
| 2008/0260804 A1 * | 10/2008 | Morris et al. ................. | 424/429 |
| 2009/0196896 A1 * | 8/2009 | Patton et al. .................. | 424/404 |
| 2009/0288908 A1 * | 11/2009 | Giroux et al. ................. | 181/131 |
| 2010/0032231 A1 * | 2/2010 | Statner et al. ................. | 181/131 |
| 2010/0056485 A1 * | 3/2010 | Park .............................. | 514/120 |
| 2010/0086580 A1 * | 4/2010 | Nyman et al. ................. | 424/423 |
| 2010/0113871 A1 * | 5/2010 | Dias et al. ..................... | 600/101 |

FOREIGN PATENT DOCUMENTS

| | | |
|---|---|---|
| EP | 1600105 A2 | 11/2005 |
| KR | 2006055894 A | 5/2006 |

* cited by examiner

*Primary Examiner* — Forrest M Phillips
(74) *Attorney, Agent, or Firm* — Price Heneveld LLP

(57) ABSTRACT

An anti-infective stethoscope is described that comprises a tube member; a head member operably connected to the tube member; and first and second earpieces operably connected to the tube member, wherein the tube member and head member include an antimicrobial barrier mechanism. The earpieces may also include an antimicrobial barrier mechanism. According to one embodiment, the antimicrobial barrier mechanism may be provided in the form of a cover comprising an antimicrobial substance wherein the cover operably covers the tube member and head member of the stethoscope. In a preferred form, the antimicrobial barrier mechanism is an antimicrobial substance applied to the tube member, head member, and optionally the earpieces.

21 Claims, 2 Drawing Sheets

STETHOSCOPE AND ANTIMICROBIAL COVER

CROSS-REFERENCE TO RELATED APPLICATION

This application claims the priority benefit of U.S. Provisional Application No. 61/220,641 filed on Jun. 26, 2009, the entire disclosure of which is incorporated herein by reference.

BACKGROUND OF THE INVENTION

The present invention generally relates to stethoscopes and to accessories for stethoscopes.

Because a doctor will use a stethoscope on different patients, it has become commonplace for the doctor's assistants to place a cloth boot over the metal end of the stethoscope that contacts the patient. This cloth boot is disposable and is replaced for each patient. It has also been recognized that the plastic tubing of the stethoscope may also come into contact with patients and, therefore, various solutions have been proposed to prevent cross-contamination of patients through the use of a stethoscope. Examples of such solutions or partial solutions are disclosed in U.S. Pat. Nos. 5,466,898, 6,575,917, and 6,520,281; U.S. Patent Application Publication Nos. 2007/0193822, and 2008/0166384; and EP 1600105 and KR 2006055894.

Specifically, U.S. Pat. No. 5,466,898 discloses a system for preventing nosocomial infection and contamination through the usage of a stethoscope, utilizing a one-usage stethoscope sleeve and fitting accessory on an off-the-shelf stethoscope such that, when the stethoscope sleeve is on the stethoscope, the head of the stethoscope is covered in its entirety as well as the body of the stethoscope up to the ear tubes. The covering of the '898 patent provides bacterial, viral, and fluid impermeable and acoustically transparent medium to cover the stethoscope head and body to the ear tubes.

U.S. Pat. No. 6,575,917 discloses a protective-sleeve-cartridge which is mounted to a stethoscope. The sleeve containing cartridge contains a series of longitudinally spaced sleeve portions which are separated by perforations. Therefore, in use, a clinician can pull on a leading end of an unused sleeve such that, the clinician can cover the head of the stethoscope with the typically disposable sleeve.

U.S. Pat. No. 6,520,281 discloses a replaceable and disposable elastomeric soft diaphragm or cover wherein the diaphragm or cover is a molded piece of elastomer, which forms an airtight seal with the stethoscope or replaces the rigid diaphragm supplied with the original stethoscope. The elastomeric stethoscope diaphragm can be impregnated with an antimicrobial agent such as silver to ensure sterility and prevent the spread of harmful bacteria to the disposable diaphragm in addition to protecting the stethoscope head from contamination.

U.S. Patent Application Publication No. 2007/0193822 discloses a stethoscope protective device for covering the head and at least a portion of the connector tube of a stethoscope. The protective device is constructed at least in part of a material that is acoustically transmissive and provides a barrier for reducing transmission of microorganisms.

U.S. Patent Application Publication No. 2008/0166384 discloses a stethoscope head cover configured to envelop a head of a stethoscope wherein the head cover can include a biocidal environment within a cavity of the cover. The cover can include an antimicrobial lining which is contiguous with the inner surface of the cover or the lining or the material of the cover can be treated or combined with a separate composition that acts as a biocidal agent. Thus, the stethoscope head can be sanitized by coming into contact with the cover member itself, the antimicrobial lining, or the biocidal agents associated therewith.

EP1600105 discloses a double stethoscope comprising two sound funnels which form a sound collection space wherein the two sound funnels are made of a soft elastic, synthetic material with added silver in the form of nano particles wherein in a sealing bead is further provided.

Finally, KR 2006055894 discloses a stethoscope in which nano silver and fragrance are included whereby the nano silver is mixed with the stethoscope material and a fragrance is also inserted into the stethoscope material. The '894 reference further includes a method of producing the same.

SUMMARY OF THE INVENTION

One aspect of the present invention is an anti-infective stethoscope for use by healthcare providers and the like having a tube member, a head member operably connected to the tube member, and first and second earpieces operably connected to the tube member. The tube member, head member and first and second earpieces include a material at least partially formed from an antimicrobial substance.

Another aspect of the present invention is an anti-infective stethoscope for use by healthcare providers and the like having a tube member, a head member operably connected to the tube member, and first and second earpieces operably connected to the tube member. The tube member and head member include an antimicrobial barrier mechanism.

Yet another aspect of the present invention is a method for making an anti-infective stethoscope comprising the steps of forming a tube member, head member and earpieces, providing an antimicrobial treatment solution, exposing the stethoscope to the antimicrobial treatment solution for an effective period of time to form covalent bonds between the antimicrobial treatment solution and the tube member, head member and earpieces; and operably connecting the tube member, head member and earpieces.

Still another aspect of the present invention is an anti-infective replaceable stethoscope component comprising: a component material shaped to engage another component of the stethoscope, wherein the component material is at least partially formed from an antimicrobial substance.

These and other features, advantages and objects of the present invention will be further appreciated by those skilled in the art upon studying the following specification, claims and appended drawings.

DETAILED DESCRIPTION OF THE PREFERRED EMBODIMENTS

Figure 1:
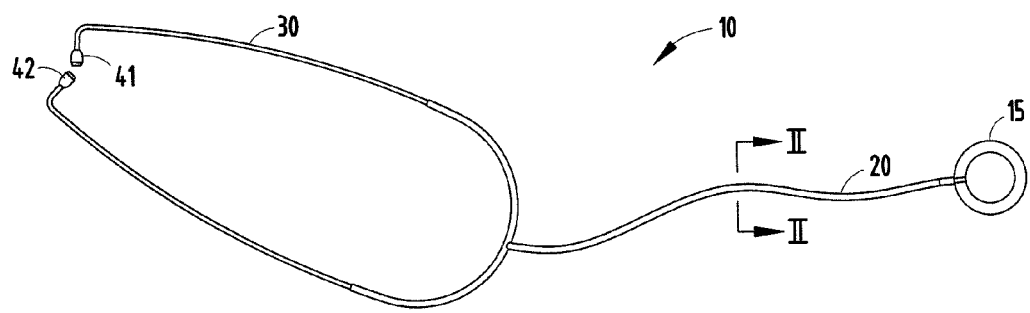
FIG. 1 is a perspective view of a stethoscope according to a first construction of the present invention.

Reference will now be made in detail to the present preferred embodiments, examples of which are illustrated in the accompanying drawings. Wherever possible, the same reference numerals will be used throughout the drawings to refer to the same or like parts.

In general, an anti-infective stethoscope is described below that comprises a tube member; a head member operably connected to the tube member; and first and second earpieces operably connected to the tube member, wherein the tube member and head member include an antimicrobial barrier mechanism. The earpieces may also include an antimicrobial barrier mechanism. According to one embodiment, the antimicrobial barrier mechanism may be provided in the form of a cover comprising an antimicrobial substance wherein the cover operably covers the tube member and head member of the stethoscope. In a preferred form, the antimicrobial barrier mechanism is an antimicrobial substance applied to the tube member, head member, and optionally the earpieces. The tube member, head member, and earpieces are components of a stethoscope that are replaceable and may be separately treated. Thus a user may, for example, wish to replace the existing earpieces with anti-infective earpieces.

Unlike the prior approaches for addressing the issue of cross-contamination, either all of the portions of the stethoscope that could come into contact with the patient comprise an antimicrobial substance, or a cover that may be retrofit onto existing stethoscopes is provided that includes an antimicrobial substance. By including the antimicrobial substance on such covers, they do not need to be disposed of each time the stethoscope is used, thereby reducing patient treatment costs.

FIG. 1 shows an anti-infective stethoscope 10 according to a first construction of the present invention. As shown, the stethoscope includes a head member 15 which is typically placed directly on a patient's body. Stethoscope 10 further includes first and second earpieces 41 and 42, respectively, which the doctor or assistant places in his or her ears. The earpieces are acoustically coupled to the head member 15 by a tube member 20 that includes tubing 22 and optionally tubing 30, which may be made of a different material than tubing 22 such as metal.

Figure 2A:
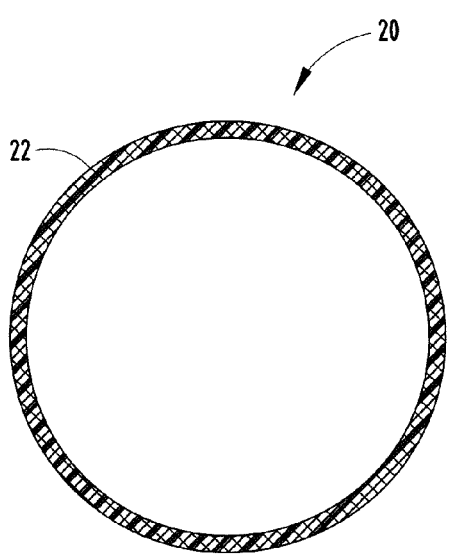
FIG. 2A is a cross-sectional view of a first embodiment of the stethoscope shown in FIG. 1 taken along line II-II.

According to a first and preferred embodiment shown in FIG. 2A, tube member 20 may comprise a polymeric tube 22 treated with, or otherwise comprising, an antimicrobial substance. For example, the tubing may be treated by spraying with or dipping in AEGIS Microbe Shield™ (from Aegis Environments, Midland, Mich.), which is copolymer of chloropropyltrihydroxysilane and octadecylaminodimethyltrihydroxysilylpropyl ammonium chloride. Other examples of suitable antimicrobial substances include Microguard® (by Microguard, Olivet, France), which is liquid solution containing hydrophilic polymers, and Microbad antimicrobial plastic additive available from Microban International. Other antimicrobial substances include 3 trimethoxysilylpropyloctadecyldimethyl ammonium chloride, hyaluronan and its derivatives, triclosan, and an organosilicon antimicrobial that is substantially free from arsenic, silver, tin, heavy metals and polychlorinated phenols. The antimicrobial substance could be copper or a silver-ion emitter. One silver-ion emitter is Germ-Gate™ (from Bovie Screen Process Co., Inc., Bow, N.H.), which is a nano particle silver based, liquid coating that can be coated onto a fabric. Another silver-ion emitter is ProtexAG (from Carolina Silver Technologies, North Carolina), which is silver-based coating that can be coated onto fabric. Yet other silver-ion emitting coatings are those available from Covalon Technologies, Ltd. of Mississauga, Ontario, Canada and Agiod antimicrobial coating available from Agion Technologies Ltd. of Wakefield, Mass. In addition, silver sodium hydrogen zirconium phosphate may be used as the antimicrobial substance. In general terms, an antimicrobial substance is capable of emitting ions that aid in the destruction of a microbe. The head member 15 or portions thereof, metal tubing 30 and earpieces 41 and 42 may also be treated with the antimicrobial substance.

The antimicrobial substance may be contained in a hydrophilic coating applied to the tube member, head member and earpieces.

Alternate antimicrobial materials may be used that are tolerant of appropriate cleaning and sterility methods. An example of which is zirconium phosphate such as Model No. XDK801 available from Xiamen Xindakang Inorganic Materials Co., Ltd. The head member 15, which contacts the patient, may be a disposable or autoclave compatible unit that can be replaced between patients or on a regular schedule. Tube member 20 can be constructed so as to be replaced and changed on a regular basis.

A preferred method for making the above described anti-infective stethoscope comprises the steps of: forming a tube member, head member and earpieces; providing an antimicrobial treatment solution; exposing the stethoscope to the antimicrobial treatment solution for an effective period of time to form covalent bonds between the antimicrobial treatment solution and the tube member, head member and earpieces; and operably connecting the tube member, head member and earpieces. The tube member, head member and earpieces may be connected before or after the stethoscope is exposed to the antimicrobial treatment solution.

Figure 2B:
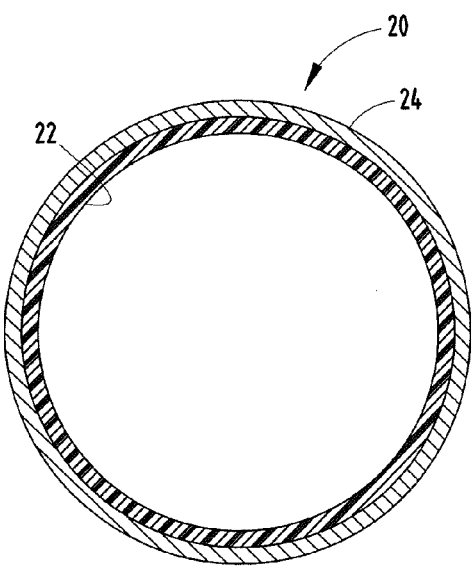
FIG. 2B is a cross-sectional view of a second embodiment of the stethoscope shown in FIG. 1 taken along line II-II.

According to a second embodiment shown in FIG. 2B, tube member 20 may comprise a polymeric tube 22 having a silver plating 24. Silver plating 24 is applied to the outer surface of polymeric tube 22 due to its antimicrobial properties. Because of this property, this embodiment has the advantage that tube member 20 may come into contact with various patients without cross-contamination as any microbes from one patient are killed by the silver. A suitable antimicrobial additive is Zeolite carrying silver, Model No. XDK101 available from Xiamen Xindakang Inorganic Materials Co., Ltd.

In addition to plating polymeric tubing 22, metal tubing 30 (if present) may be similarly plated, as may be the head (or bell) member 15 and the earpieces 41 and 42. The head member 15 includes a diaphragm that is typically made of plastic and is held in place by a plastic retaining ring. Silver, zeolite, zirconium phosphate, AEGIS Microbe Shield™, Microguard,® Germ-Gate,™ ProtexAG, Microban® or any of the other aforementioned antimicrobial substances may be plated or coated on such plastic components and on any rubberized components. Such antimicrobial materials may also be plated on the metal portions of the head member 15.

Figure 3:
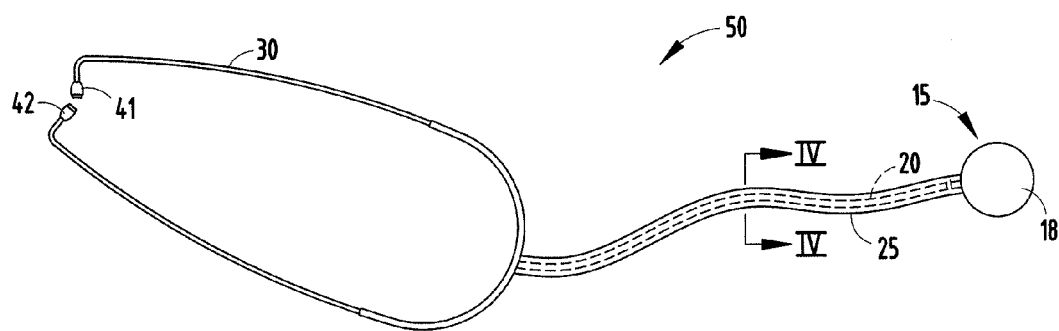
FIG. 3 is a perspective view of a stethoscope according to a second construction of the present invention.

FIG. 3 shows a stethoscope 50 according to a second construction. As shown, the stethoscope includes a head member 15 and earpieces 41 and 42 acoustically coupled to the head member 15 by tube member 20 which includes polymeric tubing 22 and optional metal tubing 30. In this construction, the polymeric tubing and metal tubing are not treated or plated. Instead, a cover 25 may be disposed around the tubing. In addition, a boot 18 may be disposed over the head portion 15.

Figure 4A:
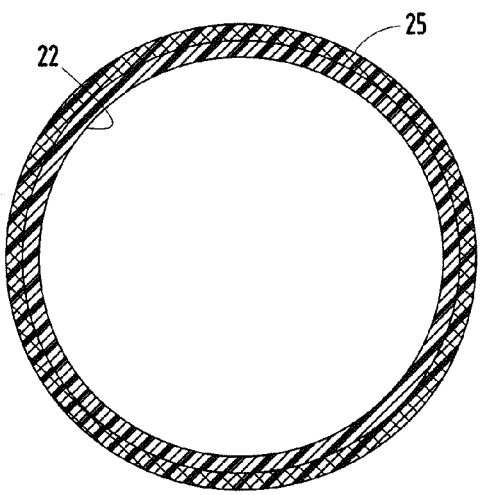
FIG. 4A is a cross-sectional view of an embodiment of the stethoscope shown in FIG. 3 taken along line IV-IV.
Figure 4B:
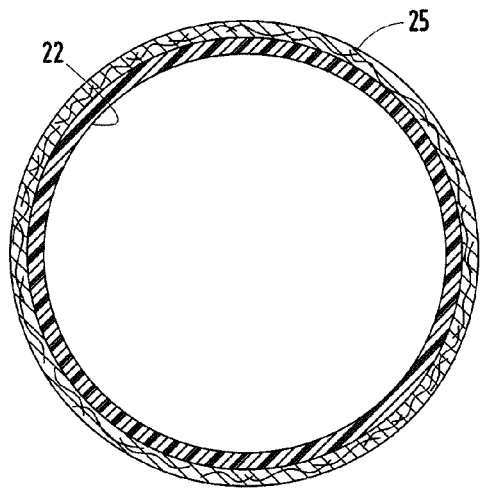
FIG. 4B is a cross-sectional view of another embodiment of the stethoscope shown in FIG. 3 taken along line IV-IV.

FIGS. 4A and 4B show two embodiments of a cover 25. In FIG. 4A, cover 25 is made of plastic film (such as polypropylene) with either a silver plating or a coating of one of the aforementioned antimicrobial substances. Cover 25 can be a polypropylene bag with elasticized ends for security.

In FIG. 4B, cover 25 is made of a nylon mesh or other polymer mesh, or cloth with either silver plating or a coating of one of the aforementioned antimicrobial substances. In this way, an existing stethoscope may be retrofit to take advantage of the antimicrobial properties of such antimicrobial substances.

In addition to the above-described materials, cover 25 can be Tyvek® with elasticized ends; a single use latex or non-latex substitute; or a silver-impregnated woven fabric type sleeve. Cover 25 may incorporate a section to protect the head member 15 that is in direct contact with the patient. This could include a tight latex or non-latex substitute cover (e.g., exam gloves).

Several covers 25 could be on the stethoscope at one time with a string or tear strip to expose a clean one below.

In any of the above embodiments, the head member 15 may also be made of, or coated with, titanium which is also an antimicrobial substance.

It will be appreciated by those skilled in the art that the above antimicrobial mechanisms may be applied to all types of stethoscopes including without limitation, standard stethoscopes and electronic stethoscopes that connect directly or wirelessly to a recording and or analysis system. An example of such an electronic stethoscope (not treated with antimicrobial substances) being the 3M™ Littmann® Electronic Stethoscope Model 3200 available from either 3M or from Zargis Medical Corp. of Stamford, Conn., who also sells a system with which the electronic stethoscope may communicate.

Further, the present invention contemplates an embodiment as that shown in FIG. 1 wherein the stethoscope components such as the earpieces 41 and 42, tubing 30, tube member 20 and head member 15 are operably releasably coupled together such that any one component may be released from the anti-infective stethoscope 10 while providing a firm attachment to the anti-infective stethoscope 10 while in use. The components may be joined together by a quick insert and quick release system that may be a snap-in place system that holds the components firmly in place while in use or it can also be a frictional engagement system that allows for firm attachment with quick release capabilities. Other quick insert and quick release systems known in the art are hereby contemplated as well.

The stethoscope components of this embodiment are exposed to an antimicrobial treatment solution such as those noted above. In this embodiment, any one component may include the quick firm attachment system such that some components may be permanent antimicrobial treated components, while others are replaceable antimicrobial treated components.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

What is claimed is:

1. An anti-infective stethoscope comprising:
a tube member;
a head member operably connected to the tube member; and
first and second earpieces operably connected to the tube member,
wherein the tube member, head member and first and second earpieces include a barrier mechanism at least partially formed from an antimicrobial substance, wherein the barrier mechanism operably covers the tube member, head member and first and second earpieces, and wherein the antimicrobial substance is capable of emitting ions that aid in the destruction of a microbe, and further wherein the antimicrobial substance is an organosilicon antimicrobial that is substantially free from arsenic, silver, tin, heavy metals and polychlorinated phenols.

2. The anti-infective stethoscope of claim 1, wherein the antimicrobial substance is contained in a hydrophilic coating applied to the tube member, head member and earpieces.

3. The anti-infective stethoscope of claim 1, wherein the antimicrobial substance comprises any one of: 3 trimethoxysilylpropyloctadecyldimethyl ammonium chloride; hyaluronan and its derivatives; triclosan; and a copolymer of chloropropyltrihydroxysilane and octadecylaminodimethyltrihydroxysilylpropyl ammonium chloride.

4. The anti-infective stethoscope of claim 1, wherein the antimicrobial substance comprises a copolymer of chloropropyltrihydroxysilane and octadecylaminodimethyltrihydroxysilylpropyl ammonium chloride.

5. An anti-infective stethoscope comprising:
a tube member;
a head member operably connected to the tube member; and
first and second earpieces operably connected to the tube member wherein the tube member and head member further comprise a cover treated with an antimicrobial substance wherein the cover operably covers the tube member and head member, and further wherein the antimicrobial substance is an organosilicon antimicrobial that is substantially free from arsenic, silver, tin, heavy metals and polychlorinated phenols.

6. The anti-infective stethoscope of claim 5, wherein the antimicrobial substance comprises any one of: 3 trimethoxysilylpropyloctadecyldimethyl ammonium chloride; hyaluronan and its derivatives; triclosan; and a copolymer of chloropropyltrihydroxysilane and octadecylaminodimethyltrihydroxysilylpropyl ammonium chloride.

7. The anti-infective stethoscope of claim 5, wherein the antimicrobial substance comprises a copolymer of chloropropyltrihydroxysilane and octadecylaminodimethyltrihydroxysilylpropyl ammonium chloride.

8. The anti-infective stethoscope of claim 5, wherein the antimicrobial substance is capable of emitting ions that aid in the destruction of a microbe.

9. A method for making an anti-infective stethoscope comprising the steps of:
forming a tube member, head member and earpieces to make up preformed stethoscope components;
providing an antimicrobial treatment solution;
exposing the preformed stethoscope components to the antimicrobial treatment solution for an effective period of time to form an antimicrobial coating by forming covalent bonds between the antimicrobial treatment solution and the tube member, head member and earpieces, and further wherein the antimicrobial substance is an organosilicon antimicrobial that is substantially free from arsenic, silver, tin, heavy metals and polychlorinated phenols; and
operably connecting the tube member, head member and earpieces.

10. The method of claim 9, wherein the antimicrobial treatment solution comprising any one of: 3 trimethoxysilylpropyloctadecyldimethyl ammonium chloride; hyaluronan and its derivatives; triclosan; and a copolymer of chloropropyltrihydroxysilane and octadecylaminodimethyltrihydroxysilylpropyl ammonium chloride.

11. The method of claim 9, wherein the antimicrobial treatment solution comprises a copolymer of chloropropyltrihydroxysilane and octadecylaminodimethyltrihydroxysilylpropyl ammonium chloride.

12. The method of claim 9, wherein the antimicrobial treatment solution is capable of emitting ions that aid in the destruction of a microbe.

13. The method of claim 9, wherein the step of operably connecting is performed after the step of exposing.

14. The method of claim 9, wherein the step of operably connecting is performed before the step of exposing.

15. An anti-infective replaceable stethoscope component comprising:
   a component material shaped to engage another component of the stethoscope,
   wherein the component material further comprises an antimicrobial barrier mechanism, and further wherein the antimicrobial barrier mechanism is an organosilicon antimicrobial that is substantially free from arsenic, silver, tin, heavy metals and polychlorinated phenols.

16. The anti-infective replaceable stethoscope component of claim 15, wherein the component is selected from the group consisting of an earpiece, a tube member, a head member and a subcomponent of a head member.

17. The anti-infective replaceable stethoscope component of claim 15, wherein the antimicrobial barrier mechanism is contained in a hydrophilic coating applied to the tube member, head member and earpiece.

18. The anti-infective replaceable stethoscope component of claim 15, wherein the antimicrobial barrier mechanism is an organosilicon antimicrobial that is substantially free from arsenic, silver, tin, heavy metals and polychlorinated phenols.

19. The anti-infective replaceable stethoscope component of claim 15, wherein the antimicrobial barrier mechanism comprises any one of: 3 trimethoxysilylpropyloctadecyldimethyl ammonium chloride; hyaluronan and its derivatives; triclosan; and a copolymer of chloropropyltrihydroxysilane and octadecylaminodimethyltrihydroxysilylpropyl ammonium chloride.

20. The anti-infective replaceable stethoscope component of claim 15, wherein the antimicrobial barrier mechanism comprises a copolymer of chloropropyltrihydroxysilane and octadecylaminodimethyltrihydroxysilylpropyl ammonium chloride.

21. The anti-infective replaceable stethoscope component of claim 15, wherein the antimicrobial barrier mechanism is capable of emitting ions that aid in the destruction of a microbe.

* * * * *